US00PP36988P2

(12) United States Plant Patent
Hoogendoorn

(10) Patent No.: US PP36,988 P2
(45) Date of Patent: Sep. 30, 2025

(54) ***HYDRANGEA* PLANT NAMED 'Perla34396'**

(50) Latin Name: *Hydrangea macrophylla*
Varietal Denomination: Perla34396

(71) Applicant: Cornelis Hoogendoorn, Zevenhuizen (NL)

(72) Inventor: Cornelis Hoogendoorn, Zevenhuizen (NL)

(73) Assignee: PERLANOVA BREEDING VOF, Zevenhuizen (NL)

( * ) Notice: Subject to any disclaimer, the term of this patent is extended or adjusted under 35 U.S.C. 154(b) by 0 days.

(21) Appl. No.: 19/010,013

(22) Filed: Jan. 5, 2025

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* plant named 'Perla34396' that is characterized by its sparse branching that makes the plant suitable to grow single stemmed plants for the use of cut flowers, its large inflorescences, its inflorescences and sterile flowers that are very firm in texture and long lasting, and its sterile flowers that are purplish pink and change to red with green centers when they fade.

2 Drawing Sheets

Botanical classification: *Hydrangea macrophylla.*
Varietal denomination: 'Perla34396'.

CROSS REFERENCE TO A RELATED APPLICATION

This application is related to a European plant breeders' rights application filed on Feb. 3, 2021, application No. 2021/0365. The information for the plant breeders' rights application was received directly from the Inventor.

BACKGROUND OF THE INVENTION

The present invention relates to a new and distinct cultivar of *Hydrangea macrophylla* and will be referred to hereafter by its cultivar name, 'Perla34396'. 'Perla34396' represents a new mophead type *Hydrangea*, a deciduous shrub grown for use as a landscape plant and for cut flowers.

'Perla34396' was derived from an ongoing breeding program conducted by the Inventor in Zevenhuizen, The Netherlands. A goal of the breeding program is to develop new cultivars of *Hydrangea macrophylla* that can be grown as single stemmed flowering hortensia.

The Inventor made a controlled cross in July of 2018 in Zevenhuizen, The Netherlands between unnamed and unpatented proprietary plants from their breeding program; female parent (ref. code 220-106-1) and male parent (ref. code 220-103-06). 'Perla34396' was selected in July of 2019 as a single unique plant amongst the resulting seedlings.

Asexual propagation of the new cultivar was first accomplished under the direction of the Inventor by softwood stem cuttings in August of 2019 in Zevenhuizen, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Perla34396' as a unique cultivar of *Hydrangea.*

1. 'Perla34396' exhibits sparse branching that makes the plant suitable to grow single stemmed plants for the use of cut flowers.
2. 'Perla34396' exhibits large inflorescences.
3. 'Perla34396' exhibits inflorescences with sterile flowers that are very firm in texture and long lasting.
4. 'Perla34396' exhibits sterile flowers that are purplish pink and change to red with green centers when they fade.

The female parent of 'Perla34396' differs from 'Perla34396' in having sterile flower sepals that are dark pink in color. The male parent of 'Perla34396' differs from 'Perla34396' in having a longer internode length and forming a more open and less branched plant habit. 'Perla34396' can be most closely compared to the *Hydrangea macrophylla* cultivars 'Bodensee' (not patented) and 'Verena' (not patented). 'Bodensee' is similar to 'Perla34396' in having leaves that are large in size and similar sterile flower coloration. 'Bodensee' differs from 'Perla34396' in having a denser branching habit making it unsuitable to grow as a single stem plant, inflorescences and sterile flowers that are smaller in size, inflorescences with less sterile flowers, and sterile flowers are softer in texture. 'Verena' is similar to 'Perla34396' in having similar leaf and sterile flower coloration. 'Verena' differs from 'Perla34396' in having weaker and longer branches, sterile flowers that are smaller in size, inflorescences with less sterile flowers, and sterile flowers that are softer in texture.

BRIEF DESCRIPTION OF THE DRAWINGS

The accompanying color photographs illustrate the overall appearance and distinct characteristics of the new

*Hydrangea*. The photographs were taken of an 18-month-old plant as grown in a greenhouse in a 19-cm container in Zevenhuizen, The Netherlands.

Figure 1:
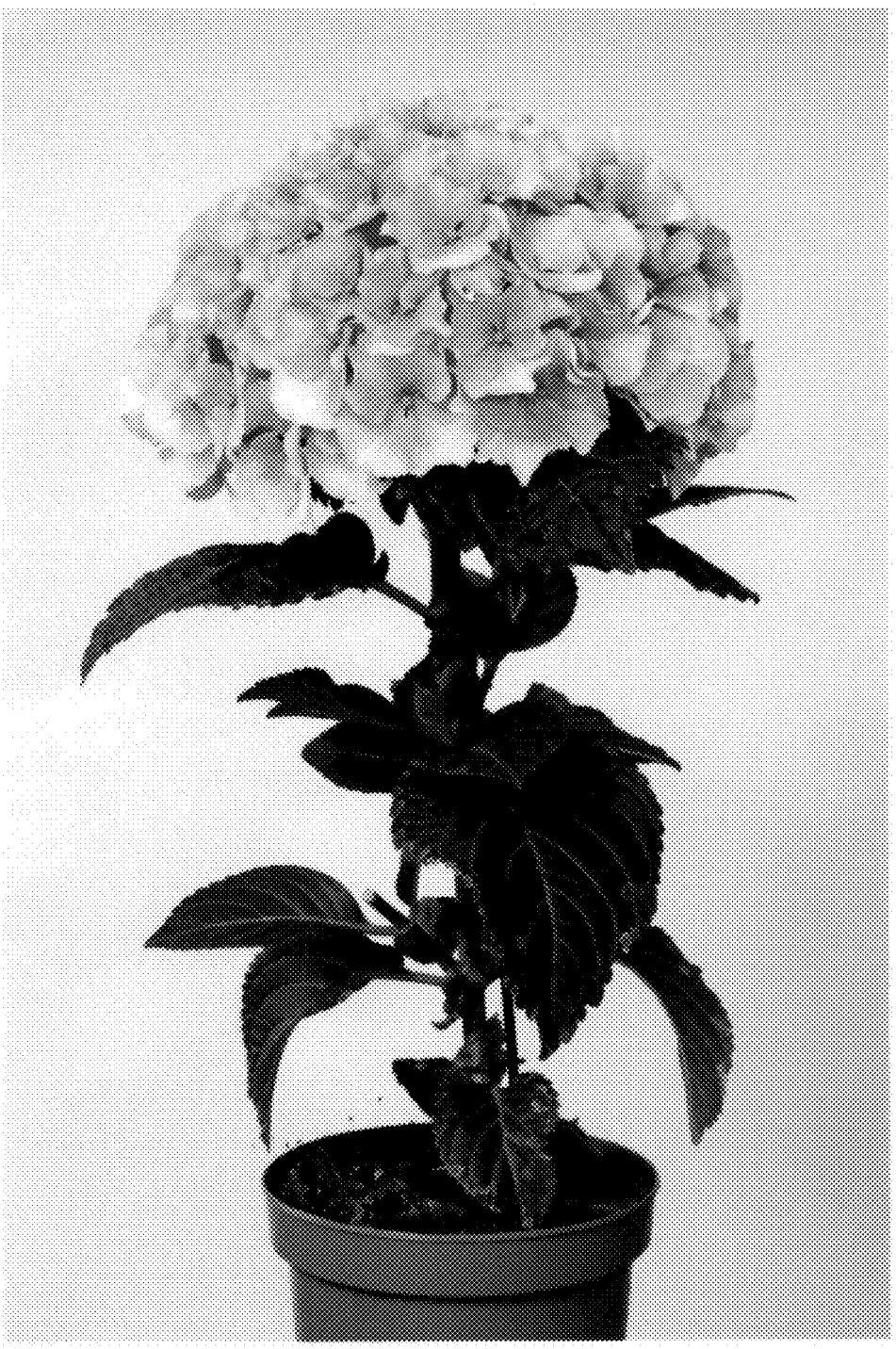

The photograph in FIG. 1 provides a side view of the plant habit of 'Perla34396' and a view of a fully opened inflorescence.

Figure 2:
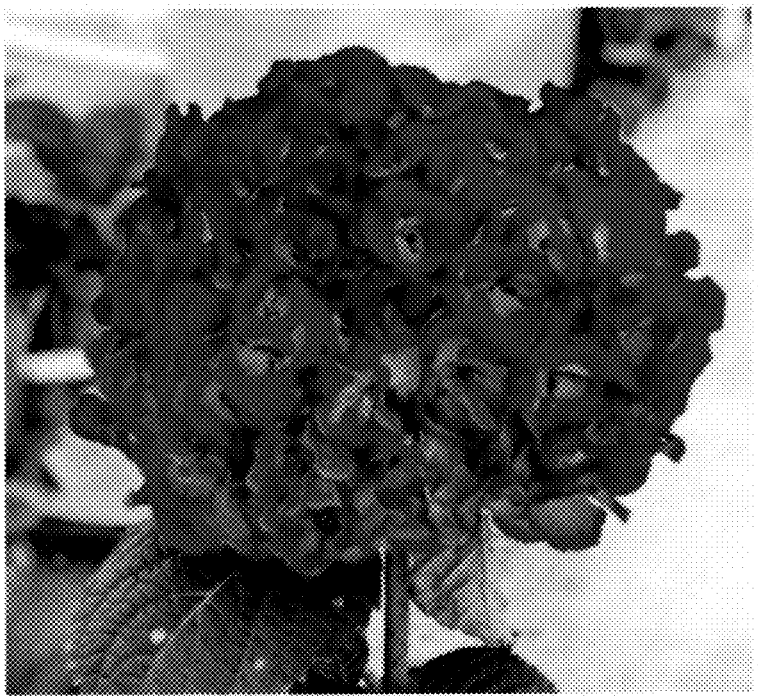

The photograph in FIG. 2 provides a close-up view of a fading inflorescence of 'Perla34396'.

Figure 3:
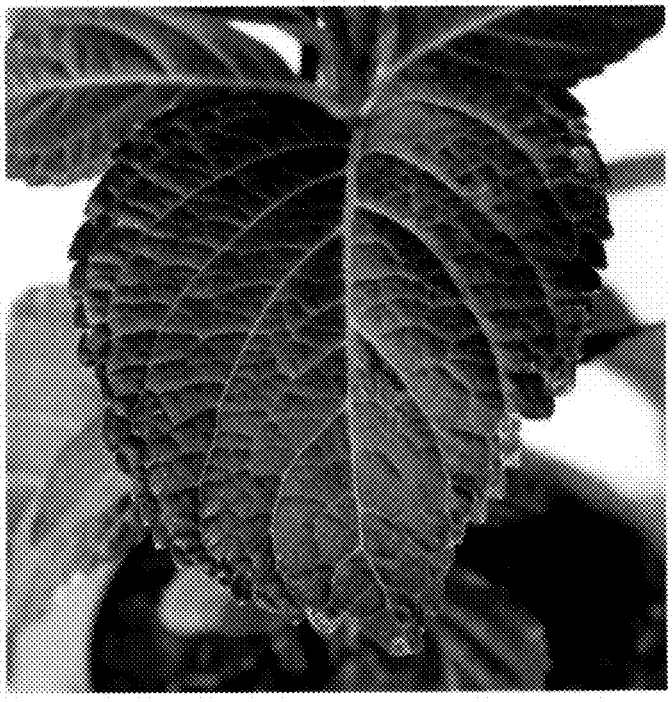

The photograph in FIG. 3 provides a close-up view of a leaf of 'Perla34396'.

The colors in the photographs may differ slightly from the color values cited in the detailed botanical description, which accurately describe the colors of the new *Hydrangea*.

BOTANICAL DESCRIPTION OF THE PLANT

The following is a detailed description of 18-month-old plants of 'Perla34396' as grown in a greenhouse in 19-cm containers in Zevenhuizen, The Netherlands. The color determination is in accordance with the Sixth Edition, 2019 reprint, Colour Chart of The Royal Horticultural Society, London, England, except where general color terms of ordinary dictionary significance are used.

General description:

*Blooming period*.—May to October in The Netherlands.

*Plant type*.—Deciduous shrub, mophead type *Hydrangea*.

*Plant habit*.—Upright, not well branched and grown as a single stemmed plant to increase inflorescence size and for suitability for cut flower production.

*Height and spread*.—Average of 55.4 cm in height, 35.6 cm in spread as an 18-month old plant grown in a container.

*Cold hardiness*.—At least in U.S.D.A. Zone 7.

*Diseases and pests*.—No resistance or susceptibility to diseases or pests has been observed.

*Root description*.—Fine and fibrous.

*Propagation*.—Softwood stem cuttings.

*Growth rate*.—Vigorous.

*Root development*.—Time required for root initiation is 4 to 5 weeks, time required to produce a young plant from rooted cutting is an average of 6 months.

Stem description:

*Stem shape*.—Rounded.

*Stem strength*.—Strong.

*Stem color*.—Young; 143C, mature; a blend of 144B and 146C.

*Stem size*.—An average of 10.5 cm in length, 7 mm in diameter.

*Stem surface*.—Younger and mature stems; glabrous, lenticellate, lenticels; dense, 5 per $cm^2$, an average of 1 mm in length, N186C in color.

*Stem aspect*.—Average angle of 35°.

*Internode length*.—Average of 7 cm.

*Branching*.—An average of 1 lateral branch per plant.

Foliage description:

*Leaf shape*.—Broadly ovate to broadly elliptic.

*Leaf arrangement*.—Opposite.

*Leaf division*.—Simple.

*Leaf base*.—Rounded.

*Leaf apex*.—Apiculate.

*Leaf margins*.—Coarsely dentate-serrate.

*Leaf venation*.—Pinnate, upper surface color; 144C, lower surface color; 146D.

*Leaf size*.—Average of 17.1 cm in length and 12.8 cm in width.

*Leaf attachment*.—Petiolate.

*Leaf surface*.—Both surfaces smooth and moderately rugose.

*Leaf color*.—Young upper surface 137A, young lower surface; 146A to 146B, mature upper surface NN137A and 147A, mature lower surface; 147B.

*Petioles*.—An average of 2.8 cm in length and 5 mm in diameter, both surfaces slightly glossy and smooth, color; upper surface 144B and 146D, lower surface 146B.

Inflorescence description:

*Inflorescence type*.—Terminal panicle, mophead in form, comprised of single sterile flowers and fertile flowers.

*Inflorescence shape*.—Flattened globular.

*Lastingness of inflorescence*.—Sterile flowers; 6 weeks, persistent, fertile flowers; 3 days, self-cleaning.

*Inflorescence number*.—One per lateral stem.

*Inflorescence size*.—Average of 20.5 cm in height, 29.4 cm in diameter.

*Flower number*.—Average of 250 sterile flowers and 50 fertile flowers per panicle.

*Flower fragrance*.—Faint, slightly moldy.

*Flower aspect*.—Sterile flowers; upright to outward, fertile flowers; upright.

*Flower size*.—Sterile flowers; an average of 6.9 cm in diameter, 2.5 cm in depth, fertile flowers; an average of 1.3 cm in diameter and 1 cm in depth.

*Flower type*.—Rotate.

*Flower buds*.—Sterile flowers; average of 1.4 cm in length, 2.1 cm in diameter, irregularly cup-shaped, color; 155C, tip 157C, fertile flowers; 6 mm in length, 5 mm in diameter, broad ovate in shape, color; 82C, tinged at top 149C, immature sepals and ovary 145A and 145B.

*Peduncles*.—Strong, average of 13.5 cm in length and 7 mm in width, color; 146C to 146D, held in a vertical angle, lateral peduncles 30° to main peduncle, surface is slightly glossy to matte, densely covered with very short soft hairs, an average of 0.2 mm in length, too small to measure color.

*Pedicels*.—Sterile flowers; moderately strong, average of 3.9 cm in length and 2 mm in diameter, average angle of 40°, color; 63B, flushed with 63A, surface is matte and densely covered with very short hairs, average of 0.2 mm in length, too small to measure color, fertile flowers; moderately strong, average of 5 mm in length and 1 mm in diameter, average angle of 25°, color; 63B, surface is very slightly glossy, densely covered with short pubescence, 0.3 mm in length, too small to measure color.

*Petals*.—Sterile flowers; 4, occasionally 5 or 6, rotate, cruciform, 5 mm in length, 3 mm in diameter, ovate to concave in shape, acute apex, cuneate base, entire margins, glabrous, smooth, matte surface, color; when opening and fully open upper surface; 75A, when opening and fully open lower surface; N75D, fertile flowers; 6, rotate, 5.5 mm in length, 3 mm in diameter, ovate to concave in shape, acute apex, cuneate base, entire margins, glabrous and matte surface, color; when opening and fully open upper surface N75B, when opening and fully open lower surface 75B.

*Sepals*.—Sterile flowers; 4, occasionally 5, reniform to broadly reniform, moderately concave in shape, strongly overlapping, rotate, cruciform in arrangement, margins crenate, apex is rounded to shallowly retuse, broadly attenuate base, average of 3.4 cm in length and 4.3 cm in width, upper and lower surface glabrous and matte, color; when opening upper and lower surface 69D, tinged 75C, when fully open upper surface 68B, top 69D, when fully open lower surface 69D, base 73C, when fading upper surface; a blend of N57A and 53B with center 144B, when fading lower surface; a blend of N57A and 53B, fertile flowers; 5, rotate in arrangement, deltoid in shape, entire margins, broad acute apex, broadly cuneate base, average of 1.75 mm in length, 2 mm in width, both surfaces are glabrous and matte, color; when opening and fully open upper and lower surface 144D.

Reproductive organs:

*Stamens*.—Sterile flowers; stamens; average of 10, varying between 8 and 12, anthers; broad oblong in shape, 1.2 mm in length and N77D in color, filaments; 6 mm in length, 64D in color, pollen; moderate in quantity, 156D in color, fertile flowers; stamens; average of 16, anthers; broadly oblong in shape, 2 mm in length and N77D in color, filaments; 5 mm in length and 70B in color, pollen; moderate in quantity and 156D in color.

*Pistils*.—Sterile flowers; pistils; average of 3, an average of 1 mm in length, stigma; club-shaped, 1 mm in length and 71B in color, style; 63C in color, 0.8 mm in length, ovary; 63D in color, fertile flowers; pistils; 3, an average of 1 mm in length, stigma; club-shaped, 71B in color, style; 8 mm in length, 63D in color, ovary; 63D in color.

*Fruit and seed*.—Not observed to date.

It is claimed:

1. A new and distinct cultivar of *Hydrangea* plant named 'Perla34396' substantially as herein illustrated and described.

* * * * *